(12) United States Patent
Ostertag et al.

(10) Patent No.: US 10,088,417 B2
(45) Date of Patent: Oct. 2, 2018

(54) APPARATUS AND METHOD FOR ANALYZING A FLOW OF MATERIAL

(71) Applicants: Hochschule Reutlingen, Reutlingen (DE); Blue Ocean Nova AG, Eschach (DE)

(72) Inventors: Edwin Ostertag, Reutlingen (DE); Tim Baeuerle, Moessingen (DE); Guenter Lorenz, Tuebingen (DE); Karsten Rebner, Reutlingen (DE); Joachim Mannhardt, Eschach (DE)

(73) Assignees: Hochschule Reutlingen, Reutlingen (DE); Blue Ocean Nova AG, Eschach (DE)

( * ) Notice: Subject to any disclaimer, the term of this patent is extended or adjusted under 35 U.S.C. 154(b) by 0 days.

(21) Appl. No.: 15/671,440

(22) Filed: Aug. 8, 2017

(65) Prior Publication Data
US 2018/0038790 A1 Feb. 8, 2018

(30) Foreign Application Priority Data
Aug. 8, 2016 (DE) .................. 10 2016 009 650

(51) Int. Cl.
*G01N 21/00* (2006.01)
*G01N 21/53* (2006.01)
*G01N 21/15* (2006.01)
*G05D 23/01* (2006.01)

(52) U.S. Cl.
CPC ............ *G01N 21/53* (2013.01); *G01N 21/15* (2013.01); *G01N 2021/155* (2013.01); *G05D 23/01* (2013.01)

(58) Field of Classification Search
CPC ...... G01N 21/538; G01N 21/15; G01N 21/53; G01N 21/274; G01N 21/534
USPC ........................................................ 356/438
See application file for complete search history.

(56) References Cited

U.S. PATENT DOCUMENTS

| 4,034,219 A | 7/1977 | Louden et al. |
| 6,196,267 B1 | 3/2001 | Rutz et al. |
| 2002/0084012 A1* | 7/2002 | Solar ............. A61M 25/09 156/51 |

(Continued)

FOREIGN PATENT DOCUMENTS

| DE | 2133 797 | 1/1973 |
| DE | 200 00 773 U1 | 4/2000 |

(Continued)

OTHER PUBLICATIONS

English Translated German Office Action dated Dec. 4, 2017.

*Primary Examiner* — Md M Rahman
(74) *Attorney, Agent, or Firm* — Muncy, Geissler, Olds & Lowe, P.C.

(57) ABSTRACT

An apparatus and method for analyzing a flow of material having an inlet region, a measurement range and an outlet region, and having a first diverter and a second diverter, and a deflection area, wherein in a first state of operation, the two diverters form a continuous first material flow space from the inlet region via the first diverter through the measurement range, via the second diverter to the outlet region, and in a second state of operation, form a continuous second material flow space from the inlet region via the first diverter through the deflection area, via the second diverter to the outlet region.

11 Claims, 11 Drawing Sheets

(56) References Cited

U.S. PATENT DOCUMENTS

| | | | |
|---|---|---|---|
| 2005/0080507 A1* | 4/2005 | Silberg | B29C 47/0876 |
| | | | 700/196 |
| 2007/0272004 A1 | 11/2007 | Rode et al. | |
| 2009/0203840 A1 | 8/2009 | Martin et al. | |
| 2012/0073687 A1 | 3/2012 | Hanson et al. | |
| 2013/0302550 A1* | 11/2013 | Tang | C08J 3/246 |
| | | | 428/40.9 |
| 2016/0052208 A1* | 2/2016 | Debora | B33Y 30/00 |
| | | | 264/40.1 |

FOREIGN PATENT DOCUMENTS

| | | |
|---|---|---|
| EP | 0 962 299 A1 | 12/1999 |
| WO | WO 02/29389 A1 | 4/2002 |

* cited by examiner

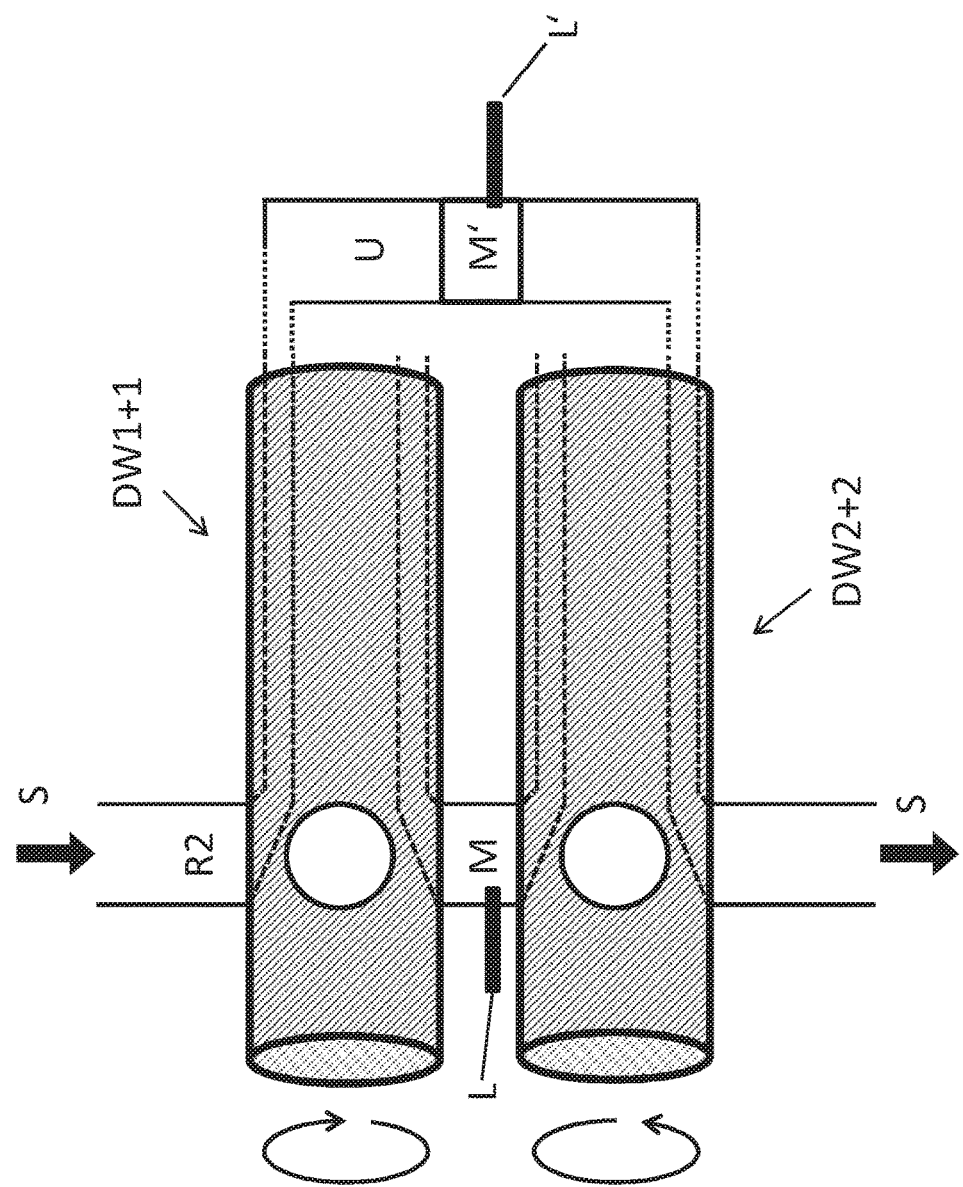

US 10,088,417 B2

APPARATUS AND METHOD FOR ANALYZING A FLOW OF MATERIAL

This nonprovisional application claims priority under 35 U.S.C. § 119(a) to German Patent Application No. 10 2016 009 650.0, which was filed in Germany on Aug. 8, 2016, and which is herein incorporated by reference.

BACKGROUND OF THE INVENTION

Field of the Invention

The present invention relates to an apparatus and a method for analyzing a flow of material.

Description of the Background Art

In many production processes, material flows must be analyzed. These can be gaseous, liquid or solid (free-flowing) material flows. Conventional methods of analysis take place without contacting the material flow, for example by means of transmission and/or reflection-based spectroscopy, by using processing windows, or by means of immersion probes applied to the flow of material or immersed therein. All analysis procedures have in common that both the probes and the measurement windows are contaminated or damaged with time, and cleaning or repair in the measurement range is not easily possible without disturbing the material flow.

SUMMARY OF THE INVENTION

It is therefore an object of the invention to provide an apparatus and a method for analyzing a flow of material which permit cleaning or repair of the measuring apparatus required for analysis without disturbing the material flow.

In an exemplary embodiment, the object is achieved according to the invention with respect to the apparatus for analyzing a flow of material in that it is provided with a material flow space and comprises, in the direction of flow: an inlet region, a measurement range designed for measuring properties of the material flow, for example a volume via an immersion probe, and an outlet region, wherein the apparatus further comprises: a first diverter, disposed between the inlet region and the measurement range, a second diverter, arranged between the measurement range and the outlet region, and a deflection area of the material flow space, which is arranged and configured such that in a first state of operation of the first diverter and the second diverter, a continuous first material flow space is formed from the inlet region via the first diverter through the measurement range via the second diverter to the outlet region, and that in a second state of operation of the first diverter and the second diverter, a continuous second material flow space is formed from the inlet region via the first diverter through the deflection area, via the second diverter to the outlet region.

Such an inventive apparatus for analyzing a flow of material provides a continuous first material flow space (from the inlet region via the first diverter through the measurement range via the second diverter to the outlet region) in the first state of operation (of the first diverter and the second diverter), through which the flow of material can flow freely, whilst the analysis of the material flow can be performed in the measurement range of said material flow space. By contrast, in the second state of operation (of the first diverter and the second diverter), a continuous second material flow space (from the inlet region via the first diverter through the deflection area via the second diverter to the outlet region) is provided, through which the material flow can flow freely, whilst the measurement range can be cleaned or repaired.

The measurement range can be formed conventionally for measuring the properties of the material flow, in particular with contactless measurements (transmission and/or reflection-based spectroscopy) or contactive measurements, applied to the material flow or probes immersed therein.

In an embodiment of the inventive apparatus for analyzing a flow of material, the first diverter is configured as a first slide diverter, which can be slid into the first material flow space between the inlet region and the measurement range and which has a first passage opening for a passage of the material flow from the inlet region via the first slide diverter into the measurement range, and which has a second passage opening for a passage of the material flow from the inlet region via the first slide diverter into the deflection area, and/or the second diverter is designed as a second slide diverter, which can be slid into the first material flow space between the measurement range and the outlet region and which has a first passage opening for a passage of the material flow from the measurement range via the second slide diverter into the outlet region, and which has a second passage opening for a passage of the flow of material from the deflection area via the second slide diverter into the outlet region, which are arranged and configured such that in each state of operation in each slide diverter in each case one passage opening faces a material flow space.

Such a slide diverter can be designed as a cylinder with respect to its outer shape. However, other external shapes, for example a cuboid shape, are also conceivable. As an alternative to a configuration as a slide diverter, one or both diverters may be designed as flap diverters, in which a reversible flap is arranged between an inlet for the material flow and two different outlets, and alternatively guides the material flow to the one or the other outlet by respectively blocking one of the two outlets.

In an embodiment, one or both diverters can also be configured as rotary diverters. Such a rotary diverter is designed as a cylinder in its outer shape. The first slide diverter described above may be replaced by a first rotary diverter, which is rotatably mounted in the material flow space between the inlet region and the measurement range, and which has a first passage opening for a passage of the material flow from the inlet region via the first rotary diverter into the measurement range, and a second passage opening for a passage of the material flow from the inlet region via the first rotary diverter into the deflection area. The second slide diverter described above may be replaced by a second rotary diverter, which is rotatably mounted in the material flow space between the measurement range and the outlet region, and which has a first passage opening for a passage of the material flow from the measurement range via the second rotary diverter into the outlet region, and a second passage opening for a passage of the flow of material from the deflection area via the second rotary diverter into the outlet region. A rotary diverter is preferably configured such that in each case the first passage opening (from the inlet region to the measurement range or from the measurement range to the outlet region) passes through the cylinder perpendicular to its main axis. The second passage opening is configured such that its inlet (to the inlet region, in the case of the first rotary diverter) or its outlet (to the outlet region, in the case of the second rotary diverter) is arranged on a circumferential circle around the cylinder of the rotary diverter, on which the inlet and outlet of the first passage opening are also situated. The inlet of the second passage opening of the first rotary diverter is preferably arranged centrally between the inlet and the outlet of the first passage opening of the first rotary diverter. Accordingly, the outlet of the second passage opening of the second rotary diverter is preferably arranged centrally between the inlet and the outlet of the first passage opening of the second rotary diverter. Both diverters are arranged and configured in such a way that in each state of operation in each rotary diverter, in each case a passage opening faces a material flow space.

In an embodiment, the inventive apparatus for analyzing a flow of material additionally comprises: a second inlet region for a second material flow; a third diverter, located between the first diverter and the measurement range; a fourth diverter, arranged between the measurement range and the second diverter; a second outlet region for the second flow of material, which are arranged and configured such that in the first state of operation of the first diverter and the second diverter, a continuous third material flow space is formed from the inlet region via the first diverter and the third diverter through the measurement range, and via the second diverter and the fourth diverter to the outlet region, wherein the second inlet region for the second material flow is closed; and that in a second state of operation of the first diverter and the second diverter, a continuous second material flow space is formed from the inlet region via the first diverter through the deflection area, via the second diverter to the outlet region, and wherein a continuous fourth material flow space is formed for the second flow of material from the second inlet region via the third diverter, through the measurement range and via the fourth diverter to the second outlet region.

In an embodiment of the inventive apparatus for analyzing a flow of material provides, in the first state of operation (of the first diverter and the second diverter), a continuous third material flow space (from the inlet region via the first diverter and the third diverter, through the measurement range, and via the second diverter and the fourth diverter to the outlet region), through which the flow of material can flow freely, whilst the analysis of the material flow can be performed in the measurement range of said material flow space. At the same time, the second inlet region for the second material flow is closed. By contrast, in the second state of operation (of the first diverter and the second diverter), a continuous second material flow space (from the inlet region via the first diverter, through the deflection area via the second diverter to the outlet region) is provided, through which the first material flow may flow freely, whilst the measurement range can be cleaned or calibrated. Therefore, in this second state of operation, a continuous fourth material flow space (from the second inlet region via the third diverter through the measurement range, and via the fourth diverter to the second outlet region) is formed, through which a second flow of material in the form of a cleaning or calibration or reference fluid can flow freely, without interfering with the first flow of material.

The third and/or fourth diverter can also be designed as a slide and/or flap diverter and/or a rotary diverter.

In an embodiment of the inventive apparatus for analyzing a flow of material, the first diverter and the third diverter are combined with each other to a first jointly shifting double diverter, and the second diverter and the fourth diverter are combined with each other to a second jointly shifting double diverter. This combination simplifies the shift from a measurement state to a cleaning, calibration or reference state of the material flow space. In this case, both or only one of the double diverters can be designed as double slide diverters, flap diverters or rotary diverters.

In an embodiment with two double rotary diverters, both double rotary diverters are designed as a cylinder in their outer shape. Analogously as described above with respect to the first rotary diverter, the first double rotary diverter has a first passage opening for a passage of the material flow from the inlet region via the first double rotary diverter into the measurement range, and a second passage opening for a passage of the material flow from the inlet region via the first double rotary diverter into the deflection area. In addition, as compared to the first rotary diverter, the first double rotary diverter has a third passage opening for a passage of a second flow of material from the second inlet region via the first double rotary diverter into the measurement range, by means of which the measurement range can be cleaned or calibrated. Analogously as described above with respect to the second rotary diverter, the second double rotary diverter has a first passage opening for a passage of the material flow from the measurement range via the second double rotary diverter into the outlet region, and a second passage opening for a passage of the flow of material from the deflection area, via the second double rotary diverter into the outlet region. In addition, as compared to the second rotary diverter, the second double rotary diverter has a third passage opening for a passage of the second flow of material from the measurement range, via the second double rotary diverter into the outlet region. The first passage opening of the first double rotary diverter and the second passage opening of the second double rotary diverter thereby correspond to the first passage opening of the first rotary diverter and the second passage opening of the second rotary diverter in terms of their design and arrangement in the cylinder, whereas the second passage opening of the first double rotary diverter is preferably designed identical to the first passage opening, albeit arranged rotated by 180° about the main axis of rotation of the cylinder. The second passage opening of the second double rotary diverter is-designed and disposed correspondingly.

In an embodiment, the second inlet region can be associated with at least one container for a cleaning fluid and/or at least one container for a calibration fluid and/or at least one container for a reference fluid.

The respective fluid can be a liquid. Alternatively or additively, gases can also be used, in particular in a combination in which a liquid is first used and thereafter a gas, preferably compressed air to blow out the material flow space, in particular, the first material flow space through which a material flow to be analyzed should then again flow, and which is not to be contaminated by otherwise possibly remaining residues of the fluid. Alternatively, a suspension (solids-laden liquid) or an emulsion (liquid-laden fluid) or an aerosol (solids-laden or liquid-laden gas) can also be used as a fluid, or in exceptional cases even free-flowing particles.

In an embodiment, the second inlet region can be connected with at least one container for the at least one cleaning fluid and with at least one container for the at least one calibration fluid and/or with at least one container for the at least one reference fluid, wherein these at least two containers can be continuously connected in each case to the second inlet region via a diverter. This can be particularly advantageously realized by means of a turret magazine which contains a plurality of containers. Alternatively, separate containers that are in each case pressurized and/or provided with a pumping apparatus can be provided, which are connected to the second inlet region in each case by means of a valve and which can provide their respective fluid by opening said valve.

In addition, it is advantageous to seal the respective material flow spaces in their diverter areas, i.e., in the areas where the diverters connect. It is preferable to provide seals which are resistant to the fluids used, in particular cleaning fluids in the form of solvents, and to the operating temperatures. Suitable in this sense are fluorine rubbers, for example, polytetrafluoroethylene, but other elastomers or metal seals, in particular metal composite seals such as metal-soft-material seals, metal-elastomer seals or metal-layer seals, or ceramic seals.

In an embodiment of the inventive apparatus for analyzing a flow of material, the measurement range is at least configured to be temperature controlled, that is, at least the measurement range can be cooled and/or heated. Such an embodiment makes it possible, for example, to carry out measurements, in particular calibration or reference measurements, at defined temperatures, in particular standard temperatures or standard temperature profiles.

In an embodiment, the measurement range can have at least partially an inner surface optimized for calibration and/or referencing. For this purpose, it has at least one surface area, which is formed in a defined, diffuse scattering or specularly reflecting manner. Preferably, this surface area is designed to be interchangeable, in particular as an interchangeable ceramic plate. In this case, a replacement can be effected in a simple manner in the second state of operation, in which the material flow is passed through the deflection area, i.e., past the measurement range. In an advantageously simple embodiment, the wall of the measurement range laterally has at least one sealable opening through which access to the measurement range is given, which, for example, allows the replacement described above, but also other measures within the measurement range. The seal of this at least one opening is necessarily closed in any operating state of the apparatus for analyzing a flow of material—that is, in the first state of operation during the measuring operation and in the second state of operation during the cleaning, calibration or referencing operation. The seal is configured such that it can only be opened when the respective operating state is interrupted, for example, in that during the second state of operation, the inflow of the individual fluids is prevented by closing the respective valves.

In an embodiment of the inventive apparatus, the apparatus can be designed for the analysis of a material flow during extrusion or extrusion molding, in particular in melt spinning, and is thus designed as an extruder module. This is preferably configured in such a way that it can be inserted in a simple manner in the discharge zone of the extruder, i.e., into the region between its feed auger and its discharge nozzle. For this purpose, the inlet region and the outlet region of the apparatus are adapted to the feed channel of the extruder, and a suitable connector is provided.

Such an extruder module allows for a simple (and subsequent) installation of the inventive apparatus for analyzing a flow of material in commercially available extruders, whereby these are equipped to carry out necessary analyses without having to interrupt the respective extrusion for the purpose of cleaning, calibration or referencing of the analysis apparatus. In an alternative embodiment, the inventive apparatus for analyzing a material flow is provided for injection molding and, therefore, designed as a module of an injection molding machine.

An object is also achieved with respect to the method for analyzing a flow of material according to the invention in that the material flow passes through a material flow space, thereby moving in the flow direction through an inlet region, a measurement range designed for measuring properties of the flow of material, and an outlet region, wherein a first diverter is disposed between the inlet region and the measurement range, a second diverter is arranged between the measurement range and the outlet region, and a deflection area for deflecting the flow of material is provided, and that in a first state of operation of the first diverter and the second diverter, the material flow is guided from the inlet region via the first diverter through the measurement range, via the second diverter to the outlet region, and that in a second state of operation of the first diverter and the second diverter, the material flow is guided from the inlet region via the first diverter through the deflection area, via the second diverter to the outlet region.

In the first state of operation (of the first diverter and the second diverter) such an inventive method of analyzing a flow of material provides a continuous first material flow space (from the inlet region via the first diverter through the measurement range, via the second diverter to the outlet region) through which the flow of material can flow freely whilst the analysis of the material flow can be performed in the measurement range of this material flow space. By contrast, in the second state of operation (of the first diverter and the second diverter), a continuous second material flow space (from the inlet region via the first diverter, through the deflection area via the second diverter to the outlet region) is provided, through which the material flow can flow freely whilst the measurement range can be cleaned or repaired.

Suitable measurement methods are, for example, spectroscopic methods, in particular transmitting and/or reflective IR (infrared, particularly NIR (Near-Infrared) or MIR (Mid-Infrared) or FIR (Far-Infrared or THz)), UV (ultraviolet), VIS (visible) or Raman spectroscopy, or fluorescence, particularly 2D fluorescence or fluorescence lifetime spectroscopy.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein:

FIG. 11 illustrates an embodiment of the invention related to the arrangement shown in FIG. 10 when using rotary diverters.

DETAILED DESCRIPTION

According to an exemplary embodiment, the inventive apparatus for analyzing a flow of material S can be configured as an extruder module, which can be used in the discharge zone of an extruder in a simple manner, that is, in the area between its auger and its discharge nozzle. For this purpose, the inlet region and the outlet region of the apparatus are adapted to the conveyor channel of the extruder, and suitable connectors can be provided.

Figure 1:
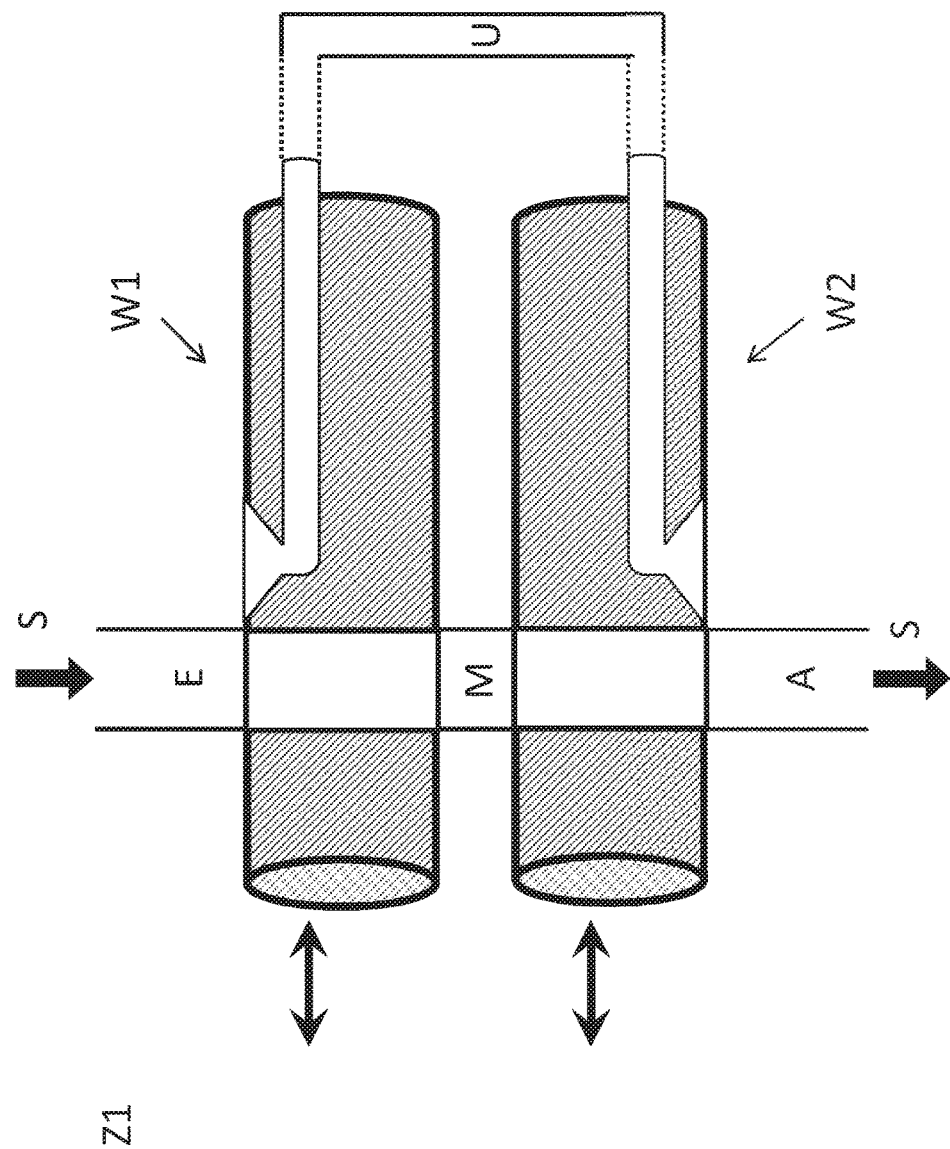
FIG. 1 illustrates an inventive apparatus for analyzing a flow of material S, with an inlet region E, a measurement range M and an outlet region A, and with a first diverter W1 and a second diverter W2 and a deflection area U in their first state of operation Z1, while a continuous first material flow space is formed from the inlet region E via the first diverter W1, through the measurement range M via the second diverter W2 to the outlet region A.
Figure 2:
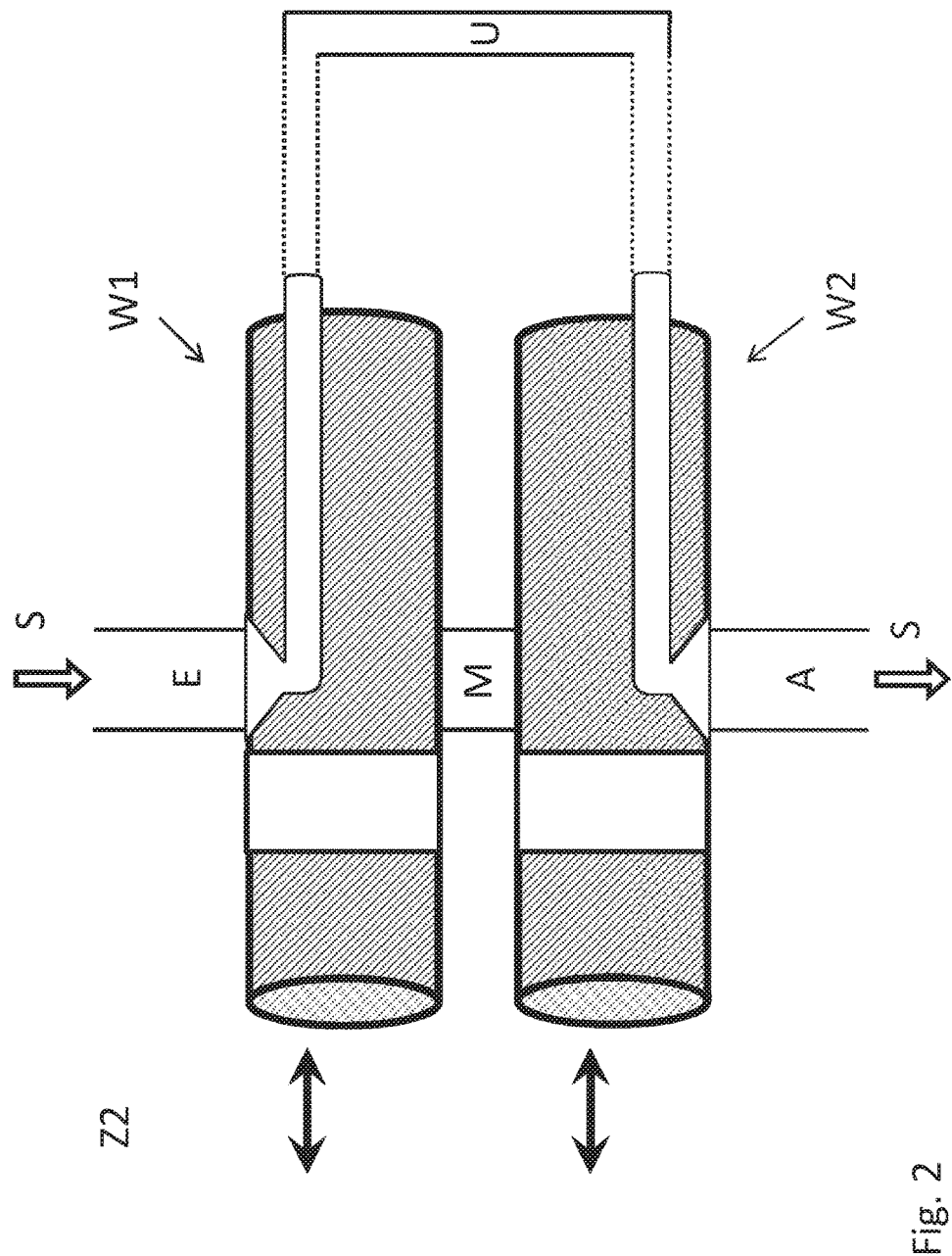
FIG. 2 illustrates the inventive apparatus for analyzing a flow of material S in its second state of operation Z2, while a continuous second material flow space is formed from the inlet region E via the first diverter W1, through a deflection area U via the second diverter W2 to the outlet region A.

FIG. 1 shows a first exemplary embodiment of the apparatus for analyzing a flow of material S, which is provided with a material flow space and has, in the flow-direction, an inlet region E, a measurement range M designed for measuring properties of the material flow S, and an outlet region A, and additionally a first diverter W1, arranged between the inlet region E and the measurement range M, a second diverter W2, positioned between the measurement range M and the outlet region A, as well as a deflection area U of the material flow space, which are arranged and configured in such a way that in a first state of operation Z1 of the first diverter W1 and of the second diverter W2, a continuous first material flow space R1 is formed from the inlet region E via the first diverter W1, through the measurement range M via the second diverter W2 to the outlet region A, whereas FIG. 2 shows the same embodiment of the apparatus for analyzing a flow of material S in a second state of operation Z2 of the first diverter W1 and of the second diverter W2, in which a continuous second material flow space R2 is formed from the inlet region E via the first diverter W1 through the deflection area U, via the second diverter W2 to the outlet region A.

Figure 3:
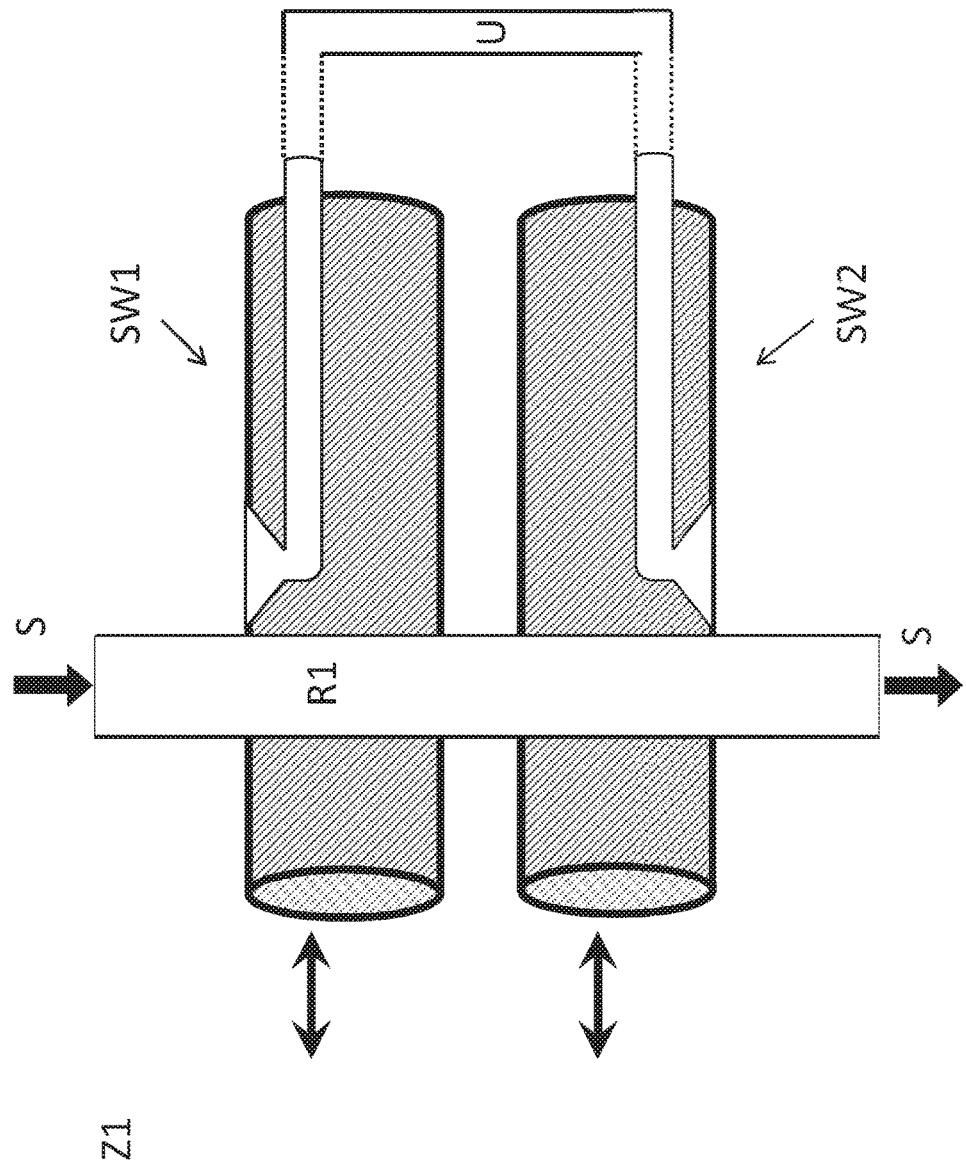
FIG. 3 illustrates the inventive apparatus for analyzing a flow of material S in its first state of operation Z1, with the continuous first material flow space R1, and formed with a first slide diverter SW1 and a second slide diverter SW2.

FIG. 3 shows a similar embodiment of the apparatus for analyzing a flow of material S, in which the first diverter is designed as a slide diverter SW1 and the second diverter is designed as a slide diverter SW2.

Figure 4:
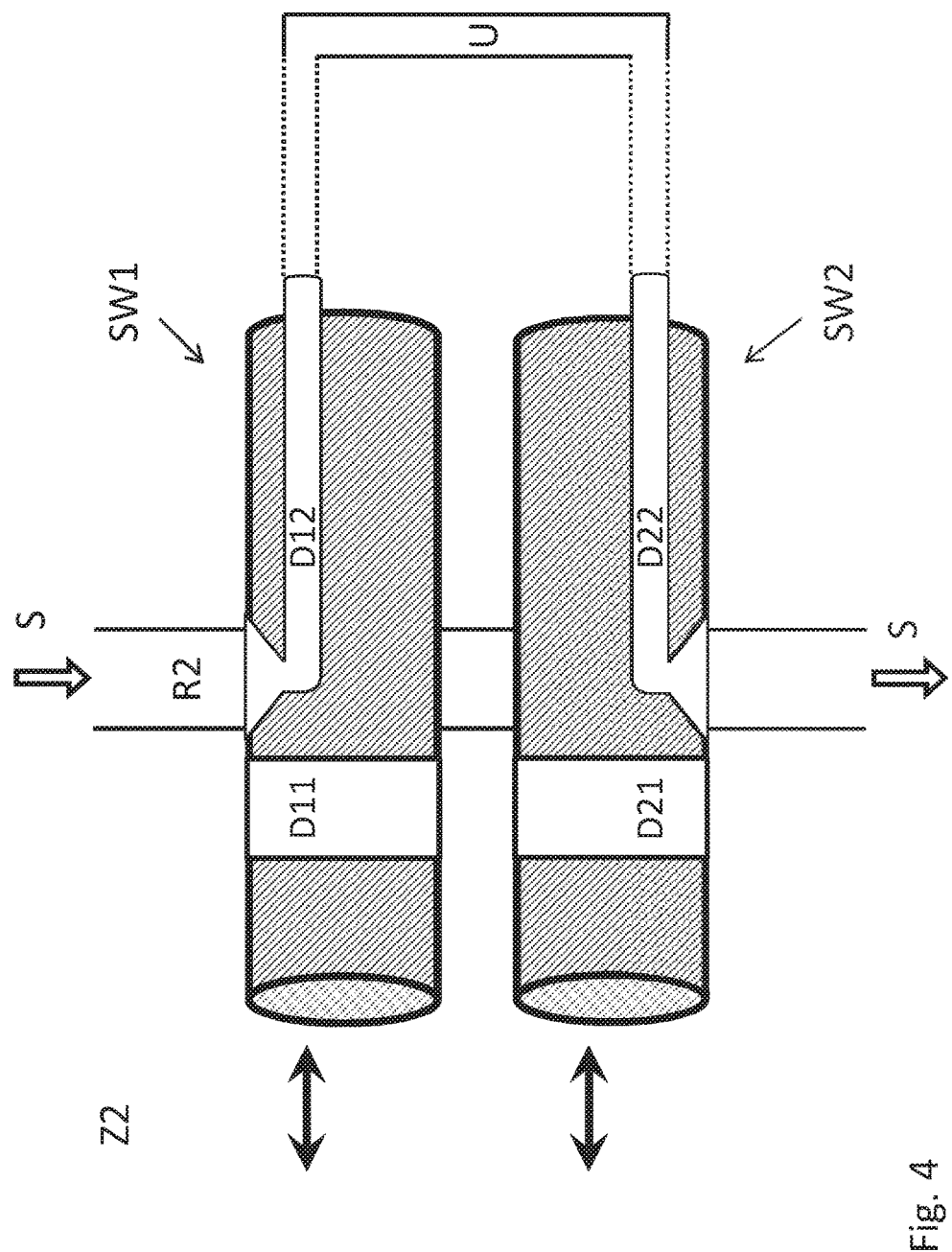
FIG. 4 illustrates the inventive apparatus for analyzing a flow of material S in its second state of operation Z2, with the continuous second material flow space R2, and formed with a first slide diverter SW1 having a first passage opening D11 and a second passage opening D12, and a second slide diverter SW2, also having a first passage opening D21 and a second passage opening D22.

FIG. 4 shows for the embodiment in FIG. 3 the first slide diverter SW1 having a first passage opening D11, which allows for the passage of the material flow S from the inlet region E via the first slide diverter SW1 to the measurement range M in the state of operation Z1 (not shown here), and having a second passage opening D12, which allows for the passage of the material flow S from the inlet region E via the first slide diverter SW1 to the deflection area U in the state of operation Z2 (shown here), and the second slide diverter SW2 having a first passage opening D21, which allows for the passage of the material flow S from the measurement range M via the second slide diverter SW2 to the outlet region A in the state of operation Z1 (not shown here), and having a second passage opening D22, which allows for the passage of the material flow S from the deflection area U via the second slide diverter SW2 to the outlet region A in the state of operation Z2 (shown here).

Figure 5:
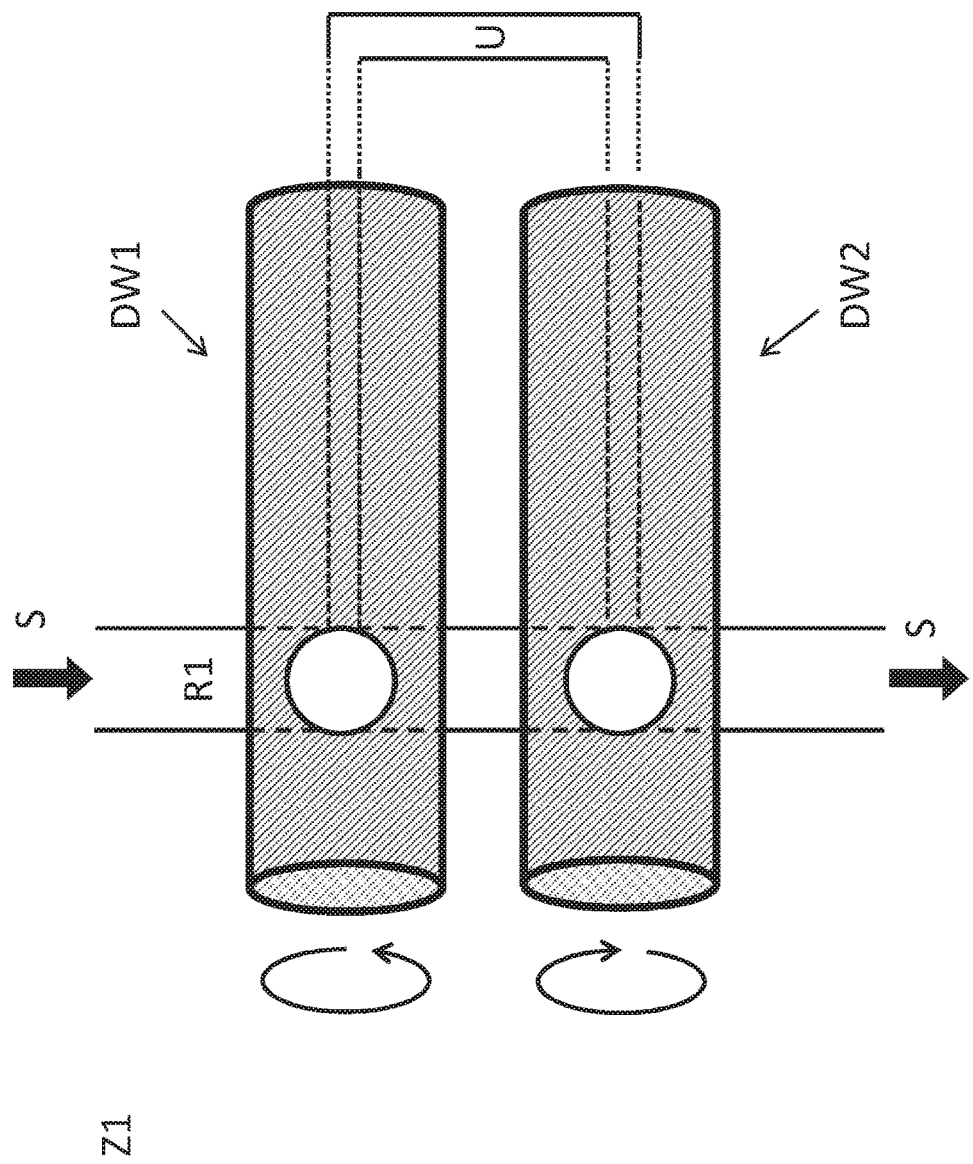
FIG. 5 illustrates the inventive apparatus for analyzing a flow of material S in its first state of operation Z1, with the continuous first material flow space R1, and formed with a first rotary diverter DW1 and a second rotary diverter DW2.

FIG. 5 shows an embodiment similar to that in FIG. 3 of the apparatus for analyzing a flow of material S in the state of operation Z1, wherein the first diverter is designed as a first rotary diverter DW1 and the second diverter is designed as a second rotary diverter DW2. A shift to the state of operation Z2 (not shown here) is effected by rotating the two rotary diverters DW1 and DW2 in the directions of rotation indicated by the respective circular arrows.

Figure 6:
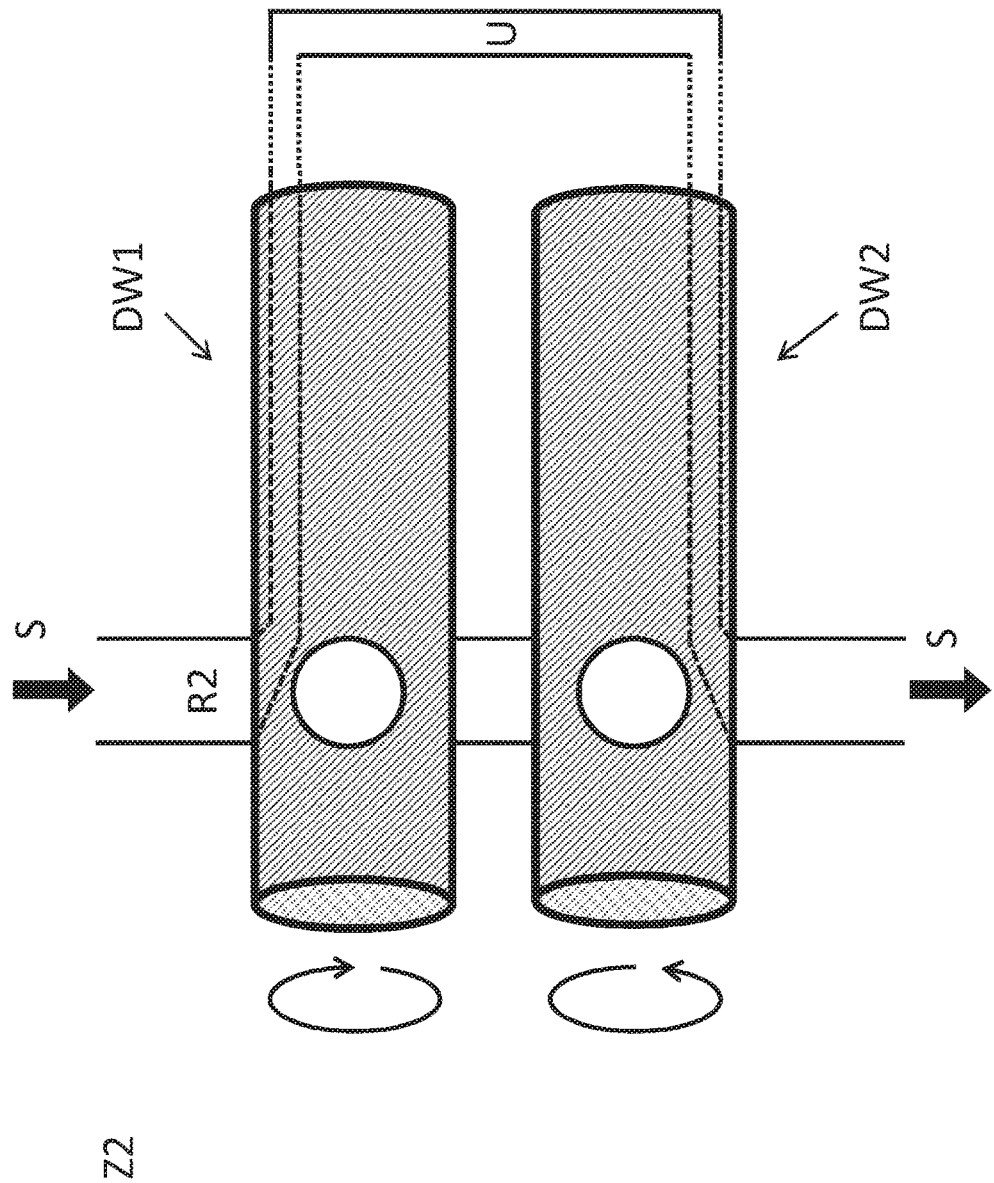
FIG. 6 illustrates the inventive apparatus for analyzing a flow of material S in its second state of operation Z2, with the continuous second material flow space R2, and formed with a first rotary diverter DW1 and a second rotary diverter DW2.

FIG. 6 shows the embodiment according to FIG. 5 in its state of operation Z2.

Figure 7:
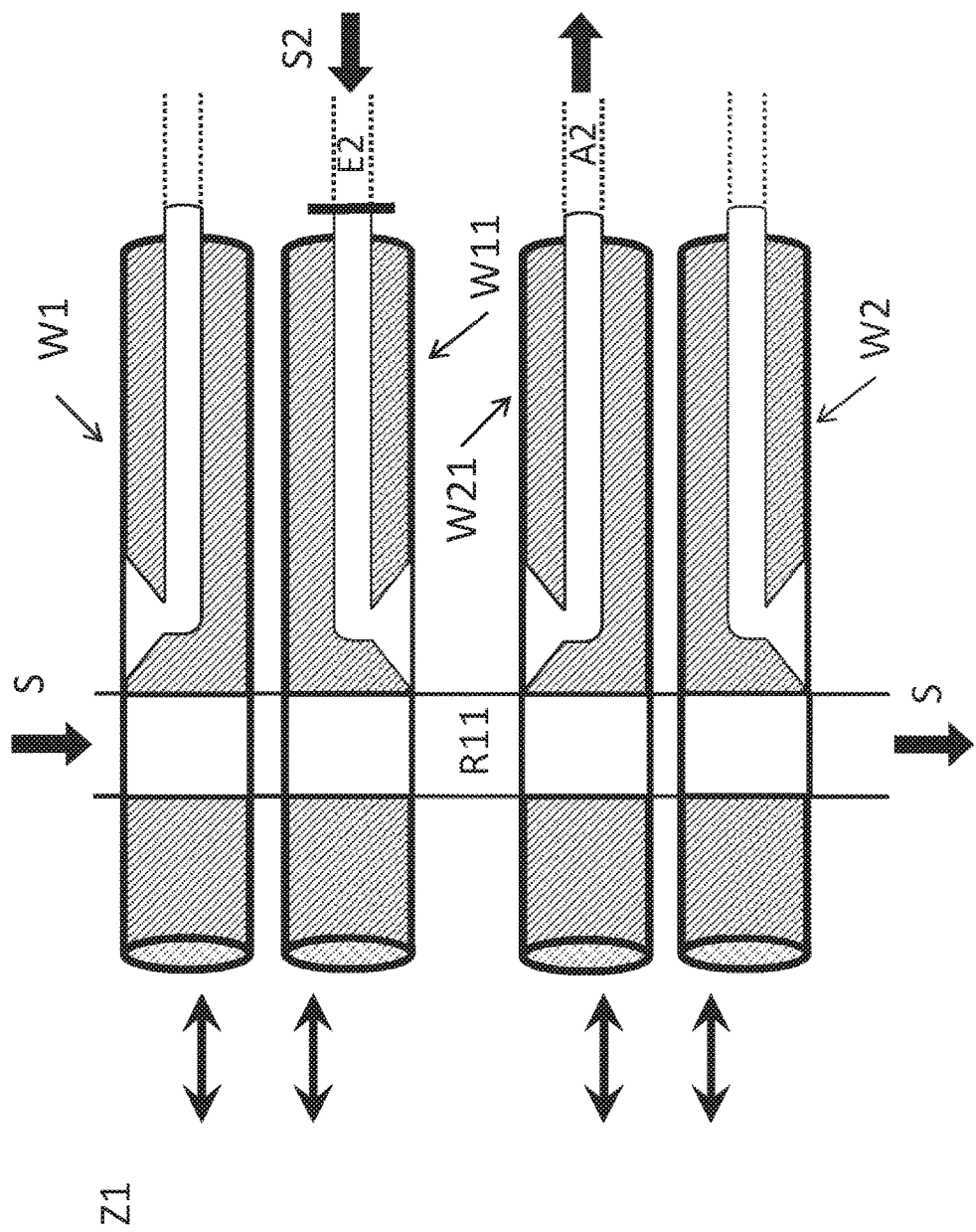
FIG. 7 illustrates an embodiment of the inventive apparatus for analyzing a material flow S in its first state of operation Z1, with a continuous first material flow space R11, comprising, in addition to the first diverter W1 and the second diverter W2, a third diverter W11 and a fourth diverter W21 as well as a second inlet region E2 and a second outlet region A2, in each case for a second material flow S2.

FIG. 7 shows a further variant, which, in addition to the components of FIG. 4 such as the first diverter W1 and the second diverter W2, has a third diverter W11 and a fourth diverter W21 and a second inlet region E2 and a second outlet region A2, respectively for a second material flow S2, and allows for the passage of the material flow S from the inlet region E via the first diverter W1 and the third diverter W11 to the measurement range M in its state of operation Z1 (shown here), and from there, via the fourth diverter W21 and the second diverter W2 to the outlet region A, thereby forming a third material flow space R11.

Figure 8:
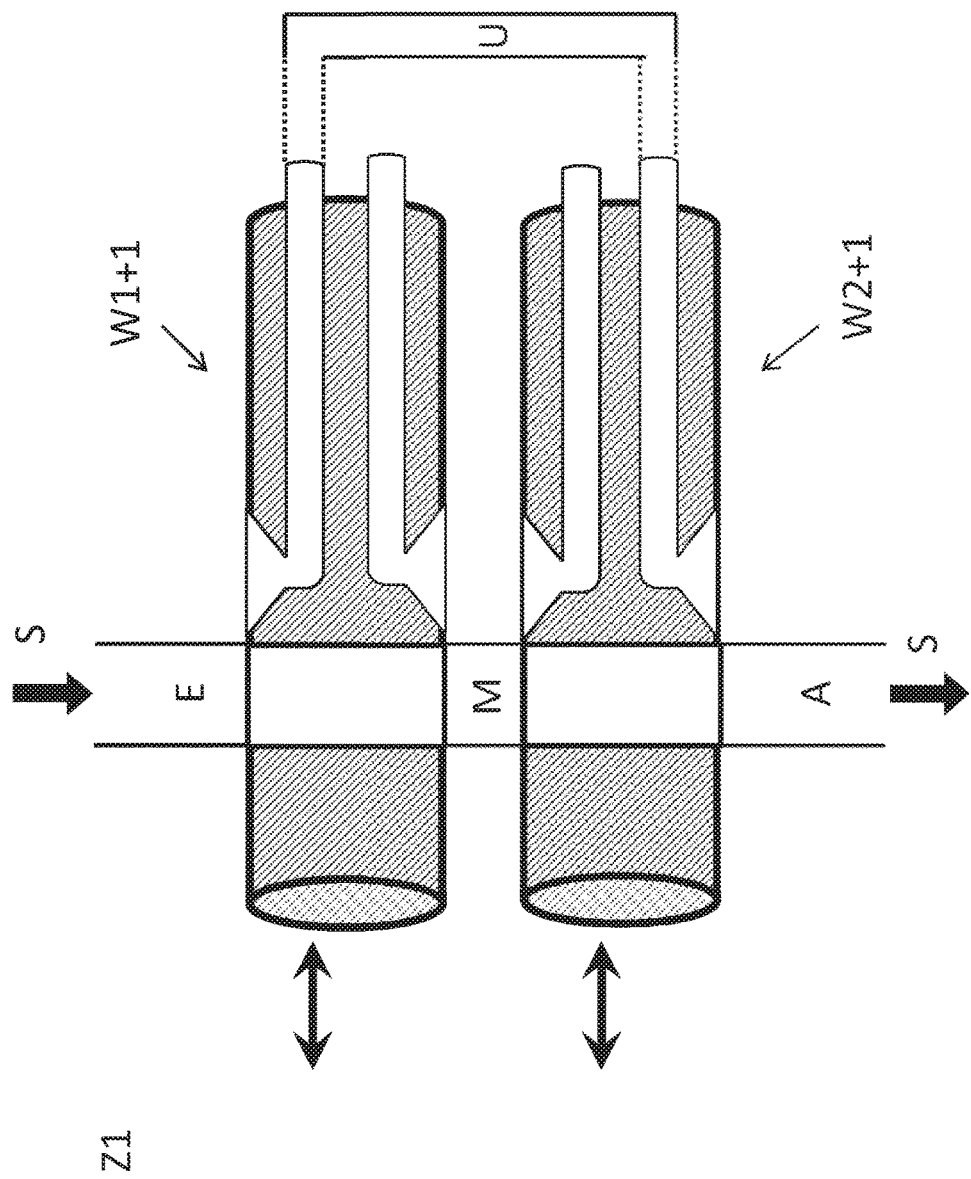
FIG. 8 illustrates an embodiment of the inventive apparatus for analyzing a material flow S in its first state of operation Z1, with a continuous first material flow space, comprising a first combination of the first diverter and the third diverter to form a first jointly shifting double diverter W1+1, and a second combination of the second diverter and the fourth diverter to form a second jointly shifting double diverter W2+1.

FIG. 8 shows a variant similar to FIG. 7, in which according to the FIG. 7, the first diverter and the third diverter are combined into a first jointly shifting double diverter W1+1, and in accordance with the FIG. 7, the second diverter and the fourth diverter are combined into a second jointly shifting double diverter W2+1. The first jointly shifting double diverter W1+1 is thereby disposed between the inlet region E and the measurement range M, and the second jointly shifting double diverter W2+1 is disposed between the measurement range M and the outlet region A. FIG. 8 shows the state of operation Z1 of the first jointly shifting double diverter W1+1 and the second jointly shifting double diverter W2+1, in which a continuous first material flow space R11 is formed from the inlet region E via a first passage opening D11 of the first jointly shifting double diverter W1+1, through the measurement range M via a first passage opening D21 of the second jointly shifting double diverter W2+1 to the outlet region A. In a second state of operation (not shown here) of the first jointly shifting double diverter W1+1 and the second jointly shifting double diverter W2+1, a continuous fourth material flow space R22 is formed from the inlet region E through a second passage opening D12 of the first jointly shifting double diverter W1+1, through the deflection area U via a second passage opening D22 of the second jointly shifting double diverter W2+1 to the outlet region A.

In this embodiment, both double diverters W1+1, W2+1 are designed as slide diverters.

Figure 9:
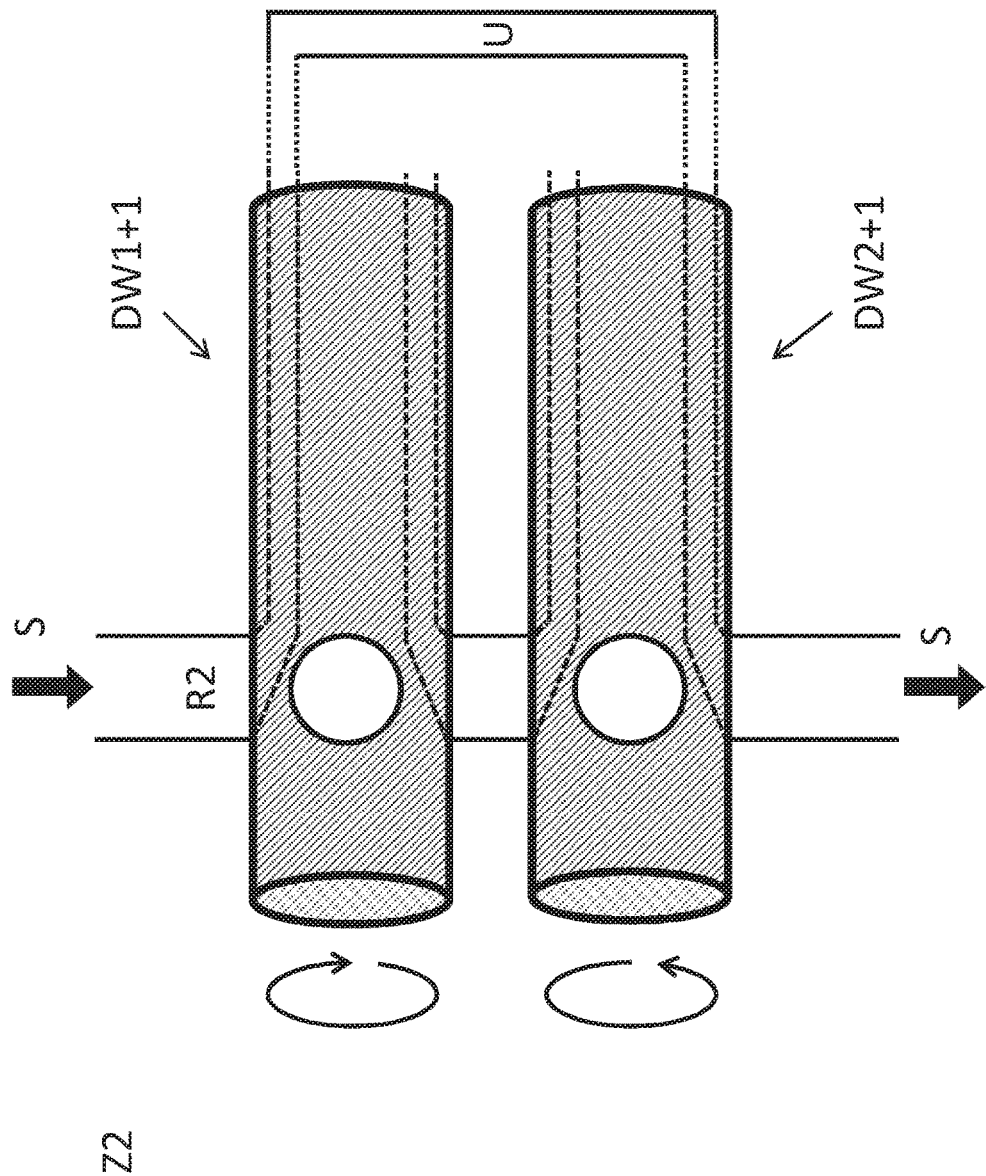
FIG. 9 illustrates an embodiment of the inventive apparatus for the analysis of a material flow S in its second state of operation Z2, with a continuous second material flow space R2, comprising a first combination of the first rotary diverter and a third rotary diverter to form a first jointly shifting double diverter DW1+1, and a second combination of the second rotary diverter and a fourth rotary diverter to form a second jointly shifting double diverter DW2+1.

FIG. 9 shows a variant similar to FIG. 8, in which both double diverters are designed as double rotary diverters DW1+1 and DW2+1 in their second state of operation Z2 with a continuous second material flow space R2.

The second inlet region E2 for the second material flow S2 (according to FIG. 7) is connected to a turret magazine, which comprises containers for a cleaning fluid, a cleaning gas, a calibration fluid and a reference fluid, as well as a control unit for controlling the turret magazine in such a way that the container required in each case faces the second inlet region E2 and is opened while the other containers are facing away and are closed.

Thus, in the second state of operation (not shown here) of the first jointly shifting double diverter W1+1 and the second jointly shifting double diverter W2+1, the second material flow S2 can be guided from the turret magazine through the second inlet region E2 and the second passage opening D12 of the first jointly shifting double diverter W1+1 into the measurement range M and from there, through the second passage opening D12 of the second jointly shifting double diverter W2+1 to the second outlet region A2.

According to this exemplary embodiment, for a cleaning of the measurement range, the control unit controls the turret magazine in such a way that first the container with the cleaning liquid is turned towards the second inlet region E2 and is opened, whereupon the cleaning liquid flows through the measurement range as a solvent, dissolving the extrudate and cleaning the range. Thereafter, the control unit controls the turret magazine in such a way that subsequently, the container with the cleaning gas is turned towards the second inlet region E2 and is opened, whereupon the cleaning gas flows through the measurement range in the form of compressed air, blowing out remaining residues of the cleaning liquid.

According to this embodiment, for calibrating the measurement range, the control unit controls the turret magazine in such a way that first, a cleaning as described above is performed and then the control unit controls the turret magazine in such a way that now the container with the calibration liquid faces the second inlet region E2 and is opened, whereupon the calibration liquid flows through the measurement range, calibrating said range by means of conventional methodology.

Accordingly, for a referencing of the measurement range, the control unit controls the turret magazine in such a way that now the container with the reference liquid faces the second inlet region E2 and is opened, whereupon the reference fluid flows through the measurement range and the reference measurement can take place.

For calibration and/or referencing, the measurement range has an optimized inner surface. This is configured as a ceramic plate which can be replaced by simple insertion, and which in its various replaceable embodiments is formed in a defined, diffuse scattering or specularly reflecting manner. A replacement can be carried out in this case in a simple manner in the second state of operation Z2, wherein the material flow S of the extrudate is passed through the deflection area U—i.e., past the measurement range M.

In this embodiment, all material flow spaces are sealed at their shifting areas, that is, at the connection areas of the diverters, with slidable seals made of fluorine rubber or other suitable materials that are resistant to solvents and operating temperatures.

Furthermore, the measurement range M is designed to be temperature controlled, which means that it can be both cooled and heated. Such a configuration allows for, for example, measurements to be performed, in particular calibration or reference measurements at defined temperatures, in particular, standard temperatures or standard temperature profiles.

According to an embodiment, the inventive method for analyzing a flow of material S in an extruder module is applied as described above, which is used in a simple manner in the discharge zone of an extruder as described above.

For this purpose, the extrudate is guided to the inlet region E and from there, it flows in a first state of operation Z1 via the first diverter W1 through the measurement range M, via the second diverter W2 to the outlet region A.

For a cleaning of the measurement range M, the extruder module is shifted to the second state of operation Z2, whereby the extrudate is guided via the first diverter W1 through the deflection area U, via the second diverter W2 to the outlet region A, while the measurement range can be cleaned without interrupting the extrusion.

The inventive apparatus and the inventive method for the analysis of a flow of material are characterized by simple integration into existing process streams.

Extrusion constitutes a preferred application for the inventive apparatus and the inventive method for analyzing a flow of material. In this respect, there has been a long time need for reliable quality control using reliable measurement of extrudate properties. However, this has so far been complicated due to frequent contamination of the measurement range and complicated modifications needed in order to carry out the required cleaning. This problem is solved by the inventive apparatus and the inventive method for analyzing a flow of material in a much simpler and faster, workable manner.

In addition, the inventive apparatus and the inventive method for the analysis of a material flow permit a simplified calibration and referencing of the measurement range.

Figure 10:
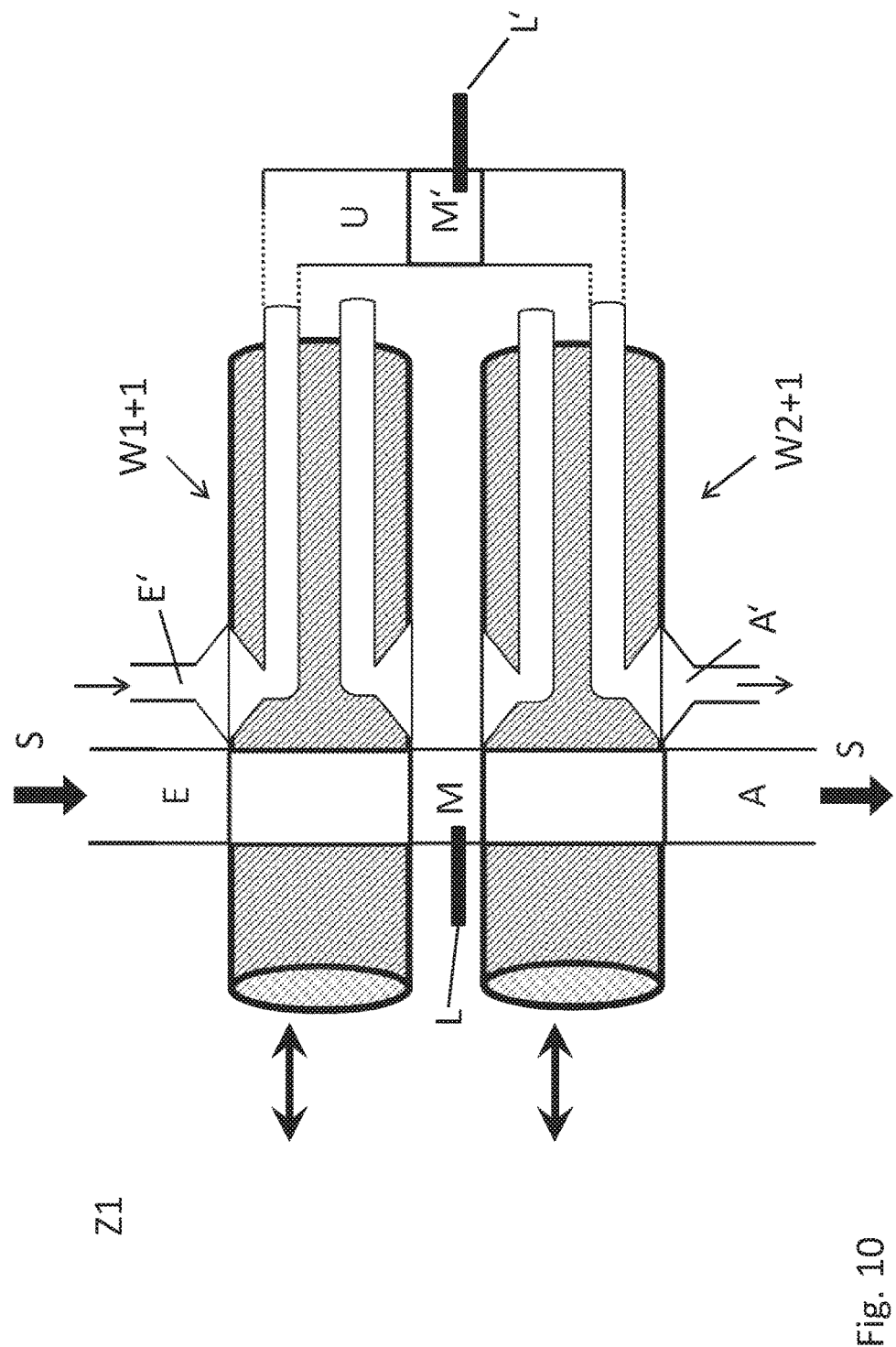
FIG. 10 illustrates an embodiment of the invention with respect to FIG. 8.

FIG. 10 shows a modified variant of the invention as compared to FIG. 8, which allows for continuous monitoring of the material flow S also during the cleaning of a measuring probe or a measurement space or during a calibration process. The arrangement shown in FIG. 10 differs from the arrangement of FIG. 8 in particular in that the deflection area U contains a further measurement range M', in which, for example, a probe L' can be introduced. In the Figure, an exemplary probe L is also shown in the measurement range M; it goes without saying that the probes shown may also be used in all the other embodiments shown and described. The probes can in particular be configured as standard ½" UNF probes, and in particular be equipped for guiding the measuring radiation with light guides, such as optical fibers.

Furthermore, the probes can be configured as immersion probes, laser probes, radar probes, ultrasonic volume measuring sensors, etc. The advantage of using probes such as those shown in FIG. 10 is in particular their easy interchangeability, for example, for maintenance purposes or for a change of, for example, a spectroscopic measurement method. Further seen in FIG. 10 are the inlet region E' and the outlet region A', through which, for example, a rinsing liquid or a calibrating medium can be supplied to the measurement range M' or discharged therefrom. In the illustrated state of operation, the material flow passes through the inlet region E, passes the measurement range M and the outlet region A, and is tested during the passage of the measurement range M in the manner already described above by a probe or other spectroscopes as regards its composition and quality. In parallel, the cleaning of the measurement range M', for example by rinsing, can be carried out with a rinsing liquid; after cleaning of M', the material flow space is available due to E', U, M' and A', in cases in which a cleaning of the measurement range M is required. In this case, the arrangement of the two diverters W1+1 and W2+1 shown is shifted in synchronism to the left until the deflection area U and the measurement range M' arranged therein can be serviced through the inlet region E. After passing through the measurement range M', the material flow S is fed to the outlet region A in this shifting position so that the outlet region is never reached by material that has not been measured.

FIG. 11 shows a variant of the invention related to the arrangement shown in FIG. 10 applicable to rotary diverters, similar to what is shown in FIG. 9. In a position of the rotary diverters DW1+1 and DW2+1 in the direction of the arrows shown, rotated by 90 degrees as compared to the illustration in FIG. 11, the flow space R2 is continuously open and the measurement range M is flowed through. In this position, the terminals, which are connected with the measurement range M', can then be in contact with a conduit for a cleaning or a calibration fluid. The connection between the rotary diverters and the second measurement space M' may, in particular, be provided by a flexible tube, a bore or a channel within the rotary diverter or the like in order to ensure a material flow or fluid flow that is free of interference, even after a rotation of the rotary diverters DW1+1 and DW2+2. Particularly advantageous in the illustrated arrangement is the ability to provide a continuous flow of material with the simultaneous cleaning of a measurement range or of a probe disposed therein.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

What is claimed is:

1. An apparatus for analysis of a material flow, the apparatus comprising:
   a material flow space;
   an inlet region;
   a measurement range designed for measuring properties of the material flow;
   an outlet region;
   a first diverter disposed between the inlet region and the measurement range;
   a second diverter arranged between the measurement range and the outlet region; and
   a deflection area of the material flow space that is arranged and configured such that:
      in a first state of operation of the first diverter and the second diverter, a continuous first material flow space is formed from the inlet region via the first diverter through the measurement range via the second diverter to the outlet region, and
      in a second state of operation of the first diverter and the second diverter, a continuous second material flow space is formed from the inlet region via the first diverter through the deflection area via the second diverter to the outlet region,
   wherein the first diverter is configured as a first slide diverter that is insertable into the material flow space between the inlet region and the measurement range, and the first diverter having a first passage opening for a passage of the flow of material from the inlet reqion via the first slide diverter into the measurement range, and the first diverter having a second passage opening for a passage of the flow of material from the inlet region via the first slide diverter into the deflection area, and/or wherein the second diverter is configured as a second slide diverter that is insertable into the material flow space between the measurement region and the outlet region, the second diverter having a first passage opening for a passage of the material flow from the measurement range via the second slide diverter to the outlet region, and the second diverter having a second passage opening for a passage of the flow of material from the deflection area via the second slide diverter to the outlet region, which are arranged and configured such that in each state of operation in the first and second slide diverter a passage opening faces the material flow space.

2. The apparatus for analyzing the flow of material according to claim 1, wherein the measurement range is configured to be temperature controlled.

3. The apparatus for analyzing the flow of material according to claim 1, wherein the apparatus is an extruder module.

4. The apparatus for analyzing the flow of material according to claim 1, wherein, in addition to the first measurement range, a further measurement range is provided that is adapted to be passed through by the material flow.

5. An apparatus for analysis of a material flow, the apparatus comprising:
   a material flow space;
   an inlet region;
   a measurement range designed for measuring properties of the material flow;
   an outlet region;
   a first diverter disposed between the inlet region and the measurement range;
   a second diverter arranged between the measurement range and the outlet region; and
   a deflection area of the material flow space that is arranged and configured such that:
      in a first state of operation of the first diverter and the second diverter, a continuous first material flow space is formed from the inlet region via the first diverter through the measurement range via the second diverter to the outlet region, and
      in a second state of operation of the first diverter and the second diverter, a continuous second material flow space is formed from the inlet region via the first diverter through the deflection area via the second diverter to the outlet region, wherein the first diverter is configured as a first rotary diverter, which is rotatably mounted in the material flow space between the inlet region and the measurement range, and which has a first passage opening for a passage of the flow of material from the inlet region via the first rotary diverter into the measurement range, and which has a second passage opening for a passage of the flow of material from the inlet region via the first rotary diverter into the deflection area, and/or wherein the second diverter is formed as a second rotary diverter, which is rotatably mounted in the material flow space between the measurement range and the outlet region and which has a first passage opening for a passage of the material flow from the measurement range via the second rotary diverter to the outlet region, and which has a second passage opening for a passage of the flow of material from the deflection area via the second rotary diverter to the outlet region, which are arranged and configured such that in each state of operation in the first and second rotary diverter a passage opening faces the material flow space.

6. An apparatus for analysis of a material flow, the apparatus comprising:
a material flow space;
an inlet region;
a measurement range designed for measuring properties of the material flow;
an outlet region;
a first diverter disposed between the inlet region and the measurement range;
a second diverter arranged between the measurement range and the outlet region; and
a deflection area of the material flow space that is arranged and configured such that:
in a first state of operation of the first diverter and the second diverter, a continuous first material flow space is formed from the inlet region via the first diverter through the measurement range via the second diverter to the outlet region, and
in a second state of operation of the first diverter and the second diverter, a continuous second material flow space is formed from the inlet region via the first diverter through the deflection area via the second diverter to the outlet region,
the apparatus further comprising:
a second inlet region for a second material flow;
a third diverter disposed between the first diverter and the measurement range;
a fourth diverter arranged between the measurement range and the second diverter; and
a second outlet region for the second material flow that is arranged and configured such that in the first state of operation of the first diverter and the second diverter a continuous third material flow space is configured from the inlet region via the first diverter, the third diverter through the measurement range via the second diverter and the fourth diverter to the outlet region, and the second inlet region is closed for the second material flow and such that in a second state of operation of the first diverter and the second diverter, a continuous second material flow space is configured from the inlet region via the first diverter through the deflection area via the second diverter to the outlet region and a continuous fourth material flow space for the second material flow is configured from the second inlet region via the third diverter through the measurement range via the fourth diverter to the second outlet region.

7. The apparatus for analyzing the flow of material according to claim 6, wherein the first diverter and the third diverter are combined to a first jointly shifting double diverter, and wherein the second diverter and the fourth diverter are combined to a second jointly shifting double diverter.

8. The apparatus for analyzing the flow of material according to claim 6, wherein the second inlet region is connected to at least one container for a cleaning fluid and/or at least one container for a calibration fluid and/or at least one container for a reference fluid.

9. The apparatus for analyzing the flow of material according to claim 8, wherein the second inlet region is connected to at least one container for the at least one cleaning fluid and at least one container for the at least one calibration fluid and/or at least one container for the at least one reference fluid, wherein the at least two containers are continuously connected via a diverter, in each case individually to the second inlet region.

10. An apparatus for analysis of a material flow, the apparatus comprising:
a material flow space;
an inlet region;
a measurement range designed for measuring properties of the material flow;
an outlet region;
a first diverter disposed between the inlet region and the measurement range;
a second diverter arranged between the measurement range and the outlet region; and
a deflection area of the material flow space that is arranged and configured such that:
in a first state of operation of the first diverter and the second diverter, a continuous first material flow space is formed from the inlet region via the first diverter through the measurement range via the second diverter to the outlet region, and
in a second state of operation of the first diverter and the second diverter, a continuous second material flow space is formed from the inlet region via the first diverter through the deflection area via the second diverter to the outlet region,
wherein the measurement range at least partially has an inner surface area optimized for calibration and/or referencing, the inner surface area being a ceramic plate having a diffuse scattering or specularly reflecting surface.

11. A method for analyzing a flow of material that flows through a material flow space and thereby passes through an inlet region, a measurement range designed for measuring properties of the material flow, and an outlet region in the direction of flow, the method comprising:
arranging a first diverter between the inlet region and the measurement range;
arranging a second diverter between the measurement range and the outlet region; and
providing a deflection area for deflecting the flow of material,
wherein, in a first state of operation of the first diverter and the second diverter, the flow of material is guided from the inlet region via the first diverter through the measurement range via the second diverter to the outlet region,
wherein, in a second state of operation of the first diverter and the second diverter, the flow of material is guided from the inlet region via the first diverter through the deflection area via the second diverter to the outlet region, wherein the first diverter is movable with respect to the material flow space between the inlet region and the measurement range, and the first diverter having a first passage opening for a passage of the flow of material from the inlet region via the first diverter into the measurement range, and the first diverter having a second passage opening for a passage of the flow of material from the inlet region via the first diverter into the deflection area, and/or wherein the second diverter is movable with respect to the material flow space between the measurement region and the outlet region, the second diverter having a first passage opening for a passage of the material flow from the measurement range via the second diverter to the outlet region, and the second diverter having a second passage opening for a passage of the flow of material from the deflection area via the second diverter to the outlet region, which are arranged and configured such that in each state of operation in the first and second slide diverter a passage opening faces the material flow space.

* * * * *